(12) United States Patent
Mohler (10) Patent No.: US 10,124,236 B2
(45) Date of Patent: Nov. 13, 2018

(54) CONCUSSION RETARDING ORTHOTIC AND METHOD OF PRODUCING THE ORTHOTIC

(71) Applicant: Christopher Edward Mohler, Beaufort, SC (US)

(72) Inventor: Christopher Edward Mohler, Beaufort, SC (US)

( * ) Notice: Subject to any disclaimer, the term of this patent is extended or adjusted under 35 U.S.C. 154(b) by 1010 days.

(21) Appl. No.: 14/278,654

(22) Filed: May 15, 2014

(65) Prior Publication Data

US 2014/0360511 A1    Dec. 11, 2014

Related U.S. Application Data

(60) Provisional application No. 61/824,799, filed on May 17, 2013.

(51) Int. Cl.
*A61C 19/045* (2006.01)
*A63B 71/08* (2006.01)

(52) U.S. Cl.
CPC .......... *A63B 71/085* (2013.01); *A61C 19/045* (2013.01); *Y10T 29/49567* (2015.01)

(58) Field of Classification Search
CPC ...... A41D 13/015; A61C 5/14; A61C 19/045; A61C 17/08; A61C 17/36; A63B 71/085;
(Continued)

(56) References Cited

U.S. PATENT DOCUMENTS 2,643,652 A * 6/1953 Cathcart ............. A63B 71/085
128/861
4,459,109 A * 7/1984 Radke ................. A61C 19/045
433/69
(Continued)

FOREIGN PATENT DOCUMENTS

WO    WO2011014965    2/2011

OTHER PUBLICATIONS

David C. Viano et al., "Effect of Mouth Guards on Head Responses and Mandible Forces in Football Helmet Impacts", Annals of Biomedical Engineering, vol. 40, No. 1, Jan. 2012.
(Continued)

*Primary Examiner* — Kari Rodriquez
*Assistant Examiner* — Camtu Nguyen
(74) *Attorney, Agent, or Firm* — B. Craig Killough; Barnwell Whaley Patterson & Helms (57) ABSTRACT

A maxillary, mandibular, or dual concussion orthotic that substantially reduces concussion resulting from forces applied to the lower jaw, and a method of producing the orthotic. The orthotic device produced according to the method described herein is objectively measured and produced to physiological parameters for an individual user. The orthotic is constructed so that the mandibular teeth are firmly indexed into the orthotic to hold the mandible in a specific position relative to the maxilla. The upper and lower jaws are positioned by the orthotic to act as a unit, and cooperate with the orthotic to effectively dissipate concussive forces and provide spacing of the temporomandibular joint, resulting in the decompression of the joint to mitigate transmission of concussive forces from the condyles of the mandible to the temporal bones of the skull.

20 Claims, 10 Drawing Sheets

(58) Field of Classification Search
CPC ......... A63B 2071/086; A63B 2071/088; A61F 5/566; A61F 5/56
USPC ........................................................ 128/861
See application file for complete search history.

(56) References Cited

U.S. PATENT DOCUMENTS

| | | | |
|---|---|---|---|
| 6,371,758 B1 | 4/2002 | Kittelsen | |
| 6,530,375 B1 * | 3/2003 | Cieslik, Jr. ............. | A61F 5/566 128/848 |
| 7,827,991 B2 | 11/2010 | Maher | |
| 7,882,839 B2 * | 2/2011 | Ambis, Jr. ........... | A63B 71/085 128/861 |
| 8,113,206 B2 | 2/2012 | Roettger et al. | |
| 2006/0011204 A1 * | 1/2006 | Maher .................... | A61F 5/566 128/861 |
| 2011/0264017 A1 * | 10/2011 | Smernoff ............. | A61C 9/0006 601/38 |
| 2012/0271190 A1 * | 10/2012 | Mortensen ........... | A61B 5/0488 600/546 |

OTHER PUBLICATIONS

Clayton A. Chan, Norman R. Thomas, "Clinical and Scientific Validation for Optimizing the Neuromuscular Trajectory using the Chan Protocol", Jul. 21, 2004.

Barry C. Cooper & Israel Kleinberg, Establishment of a Temporomandibular Physiological State with Neuromuscular Orthosis Treatment Affects Reduction of TMD Symptoms in 313 Patients, The Journal of Craniomandibular & Sleep Practice, Apr. 2008, vol. 26, No. 2.

Barry C. Cooper, Temporomandibular Disorders: A Position Paper of the International College of Cranio-Mandibular Orthopedics (ICCMO), The Journal of Craniomandibular Practice, Jul. 2011, vol. 29, No. 3.

Nicolae Chipaila, Fabrizio Sgolastra, Alessandro Spadaro, Davide Pietropaoli, Chiara Masci, Ruggero Cattaneo, Annalisa Monaco, The effects of ULF-TENS stimulation on gnathology: the state of the art, The Journal of Craniomandibular & Sleep Practice, 2014 vol. 32, No. 2.

Tjerk Weggen, Hans-Jurgen Schindler, Alfons Hugger, Effects of myocentric vs. manual methods of jaw position recording in occlusal splint therapy—a pilot study, Journal of Craniomandibular Function, 2011, 3(3):177-203.

* cited by examiner

CONCUSSION RETARDING ORTHOTIC AND METHOD OF PRODUCING THE ORTHOTIC

FIELD OF THE INVENTION

This invention relates to medical devices generally and is more specifically related to a maxillary or mandibular concussion retarding orthotic.

BACKGROUND OF THE INVENTION

Concussions are a problem associated with physical activities. Athletes, soldiers and others involved in strenuous activities, and particularly activities that involve physical contact, are subject to concussions and associated traumatic brain injury. A concussive force as low as 40 Gs may result in concussive force to even healthy, normally developed persons.

According to a study, 90% of concussions resulting in unconsciousness are the result of blows to the lower jaw. Collapsed bite caused by temporomandibular disorders (TMD) is a risk associated with concussion. It has been estimated that 65% of American adults have TMD, and that an even higher percentage adult athletes have TMD. These disorders place such persons at a higher risk for concussion resulting from forces introduced through the lower jaw.

There is a need for an orthotic that will substantially reduce the likelihood of concussion caused by forces introduced to the lower jaw. The orthotic should be effective in environments experienced by persons subjected to concussive forces to the lower jaw, such as forces encountered by football players and soldiers. Previously known and used mouth guards do not physiologically relate the mandible to the cranium, do not adequately protect the mandible from forces, and do not minimize the transfer of forces from the mandible to the head and neck, which reduces the ability of such devices to dissipate concussive forces.

SUMMARY OF THE INVENTION

The present invention is maxillary, mandibular, or dual concussion orthotic that substantially reduces concussion resulting from forces applied to the lower jaw, and a method of producing the orthotic. The invention reduces forces associated the condyle of the mandible relative to the temporal bone of the skull.

A specific, optimal position of the mandible for the purposes of the invention is unique to every individual. The orthotic device produced according to the method described herein is objectively measured and produced to physiological parameters for a specific individual user.

The orthotic is constructed so that the mandibular teeth are firmly indexed into the orthotic to hold the mandible in position relative to the maxilla. The upper and lower jaws are positioned by the orthotic to act as a unit, and cooperate to effectively dissipate concussive forces. The orthotic provides increased spacing of the temporomandibular joint, resulting in the decompression of the joint. The orthotic thereby mitigates transmission of concussive forces from the condyles of the mandible to the temporal bones of the skull.

DESCRIPTION OF PREFERRED EMBODIMENTS

The present invention is a maxillary, mandibular, or dual arch concussion orthotic, and a method of producing the orthotic. The orthotic is preferred to be fabricated of a flexible and resilient material that will absorb forces, but which will also firmly position the mandible relative to the maxilla as required by the goals of the invention. The orthotic materially reduces the incidence of concussions caused by driving the condyle of the mandible into the temporal bone of the skull, with the orthotic substantially reducing or eliminating the transfer of concussive forces from the condyle to the temporal bone. The oral appliance of the invention stabilizes the upper jaw, lower jaw, and right and left temporomandibular joints, and reduces the articular discs downwardly and forward relative to the articular eminence of the skull.

There is a specific position of the human jaw that allows the body to materially reduce strains, torques and skews. The specific position is a precise point in space that can be measured using computerized jaw tracking instrumentation. In most cases, accuracy of 0.1 to 0.3 millimeters is required for the desired result. In a preferred embodiment, an optimized bite definition of the subject is obtained while stabilizing the upper jaw, lower jaw, and right and left temporomandibular joints.

Figure 1:
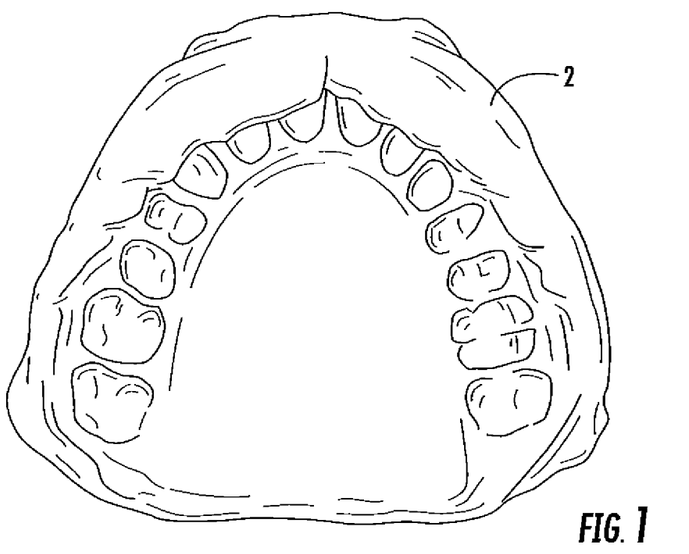
FIG. 1 is a plan view of a dental impression taken before positioning of a subject's mandible to the optimal position.

A preferred method of producing the dental orthotic of the invention is described. Upper and lower impressions 2 of the teeth are taken to produce dental models 4, 6. Accurate maxillary and mandibular impressions 2 are taken of the teeth of the upper and lower jaw for production the custom maxillary, mandibular, or dual arch orthotic. FIG. 1. The impression may be taken in polyvinyl siloxane (PVS).

Figure 2:
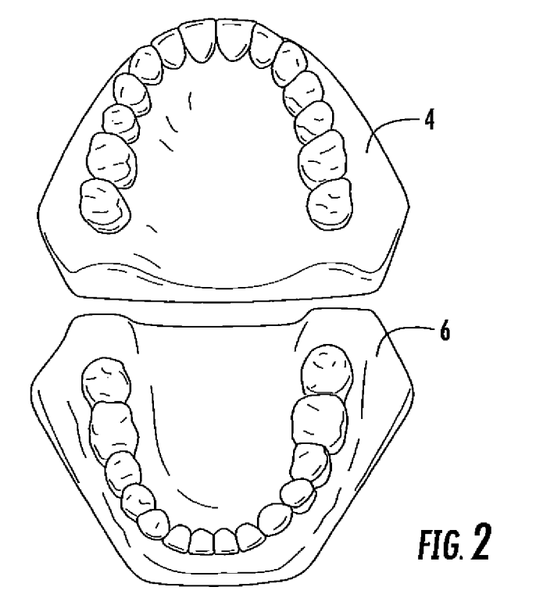
FIG. 2 shows models of a subject's teeth made from impressions.
Figure 3:
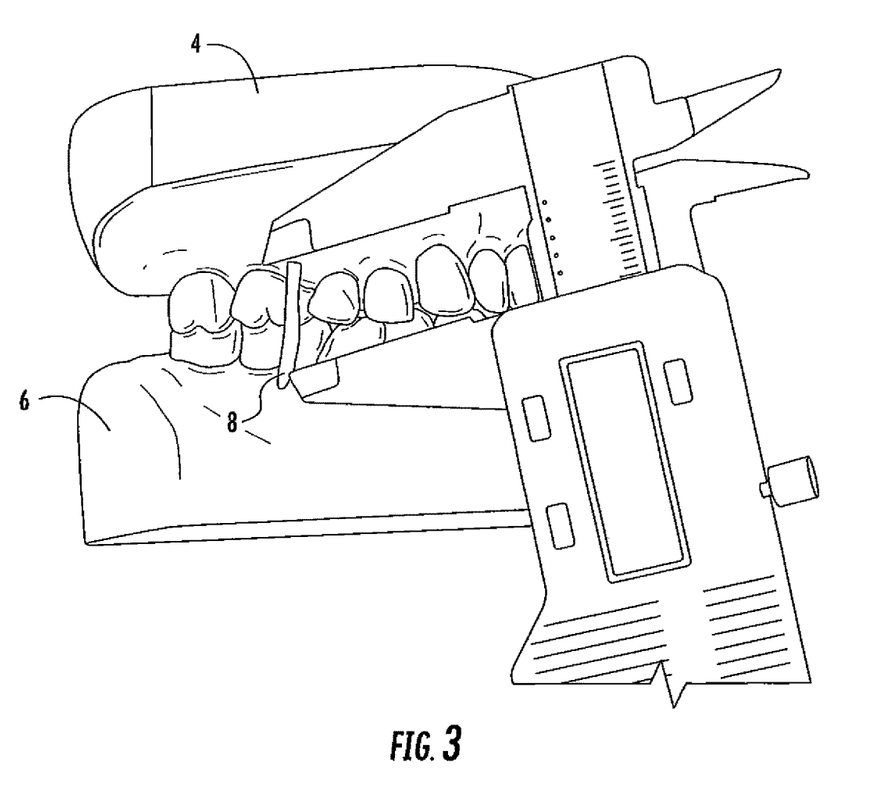
FIG. 3 demonstrates taking measurements from the models.

Upper and lower models 4, 6 of the teeth are produced from the impressions 2. FIG. 2. Measurements are taken of the models with the teeth of the models interdigitated. FIG. 3. A line 8 is drawn on each side of the models and anteriorly that extends from the upper teeth to the lower teeth. Movement of the position of the mandible relative to the maxilla can be visually identified after repositioning of the jaw according to the method. Movement front and back and side to side is demonstrated by the position of the lines after the orthotic is installed.

Figure 4:
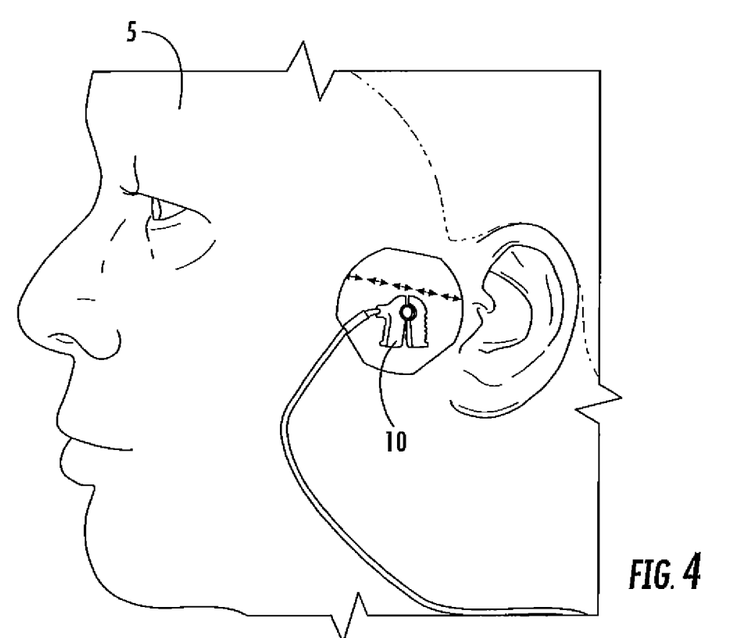
FIGS. 4 and 5 show attachment of a TENS unit to a subject.
Figure 5:
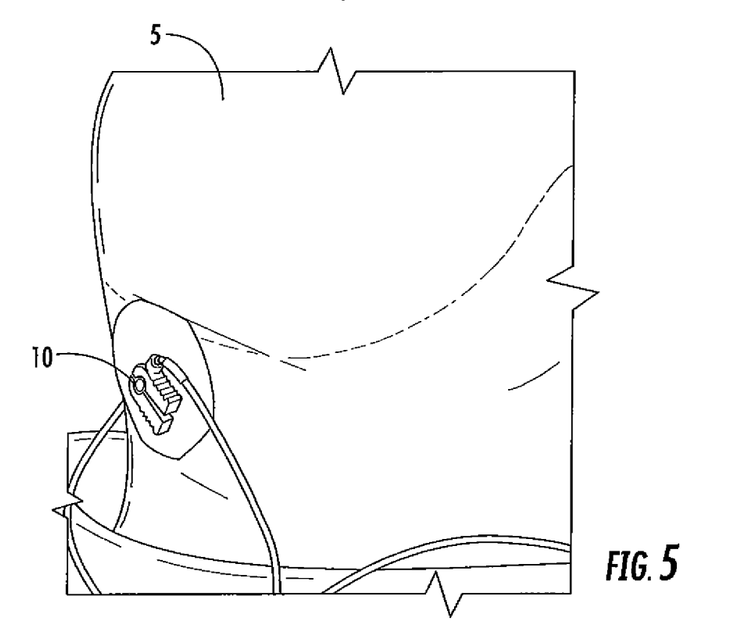

Positioning of the mandible and the associated condyles as required by the invention is best obtained when the head and neck muscles are relaxed. It is therefore preferred that these muscles are subjected to stimulation such as stimulation by ultra-low frequency transcutaneous electrical neural stimulation (TENS) unit 10. FIG. 4; FIG. 5.

The unit is preferred to be connected to the subject 5 on each side at about the temporomandibular joint, and also at the back of the subject's head. It is preferred that the connection to the TENS unit continue for a minimum of 45 minutes to adequately relax masticatory muscles to their physiologic resting length. The amplitude of the TENS unit is set at clinical threshold, balancing the involuntary left and right stimulus.

The TENS provides involuntary neuromuscular stimulation to the masticatory muscles that are associated to the muscles of the head and neck, and provide physiologic length to these postural muscles. Cervical neck muscles affect the posture of the head and neck. The TENS process according to the invention also relaxes the cervical neck muscles and allows the head and neck to come to a more physiologic posture. The resulting posture provides proper positioning for custom construction of the orthotic.

Figure 6:
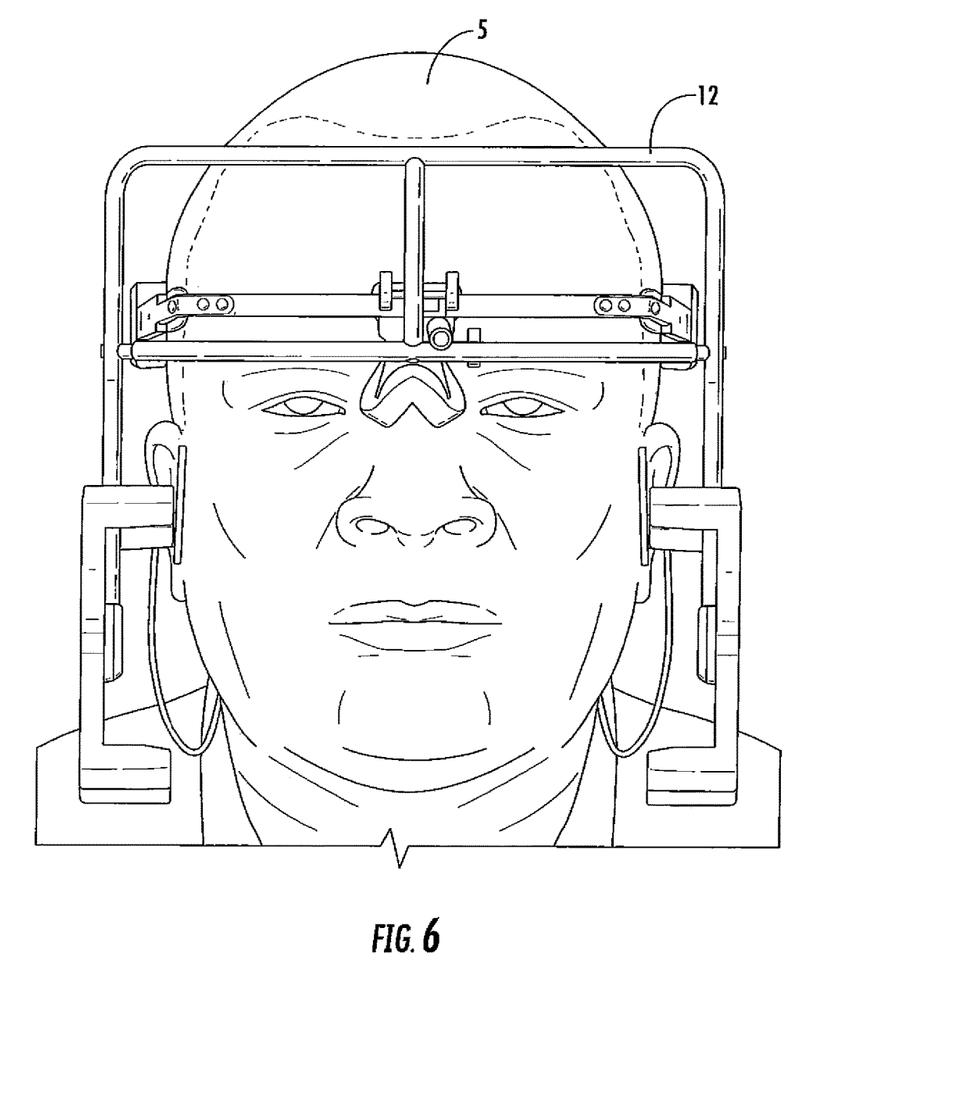
FIG. 6 demonstrates use of a jaw tracking kinesiograph.

A computerized jaw tracking kinesiograph 12 framework is placed over the subject's head in a preferred embodiment of a method of the invention. FIG. 6. The jaw tracking kinesiograph senses the spatial location of a permanent magnet that is mounted, for example, on the mandibular incisors. A set of magnetometers sense displacement of the magnet in three planes. The sensors are carried on a light framework supported by a device which is worn by the subject in and stabilized, such as by an elastic strip behind the head. The framework is arranged about the magnet and oriented to a desired position of the subject before recordings are taken. Signals derived from the device are based on voltages representing vertical, lateral, and anteroposterior jaw movement. The voltages are referenced to the planes of orientation of the magnetometers.

Figure 8:
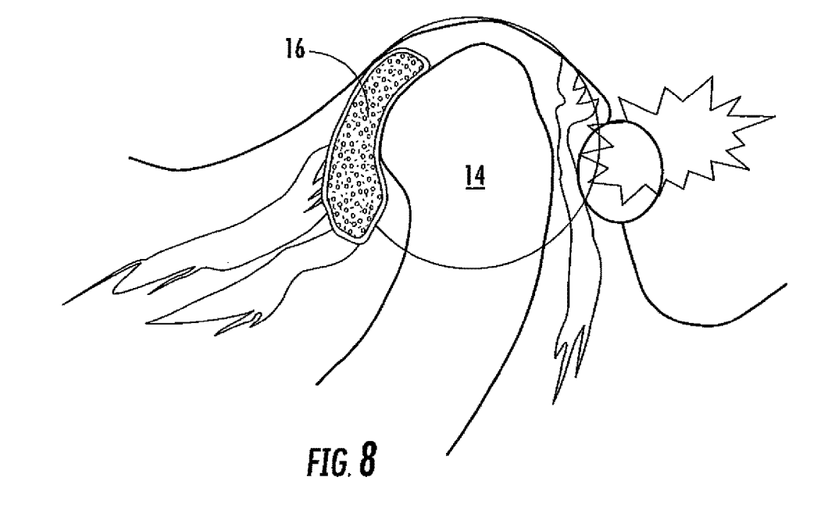
FIG. 8 shows a condyle positioned relative to the temporal bone prior to repositioning according to the method.
Figure 9:
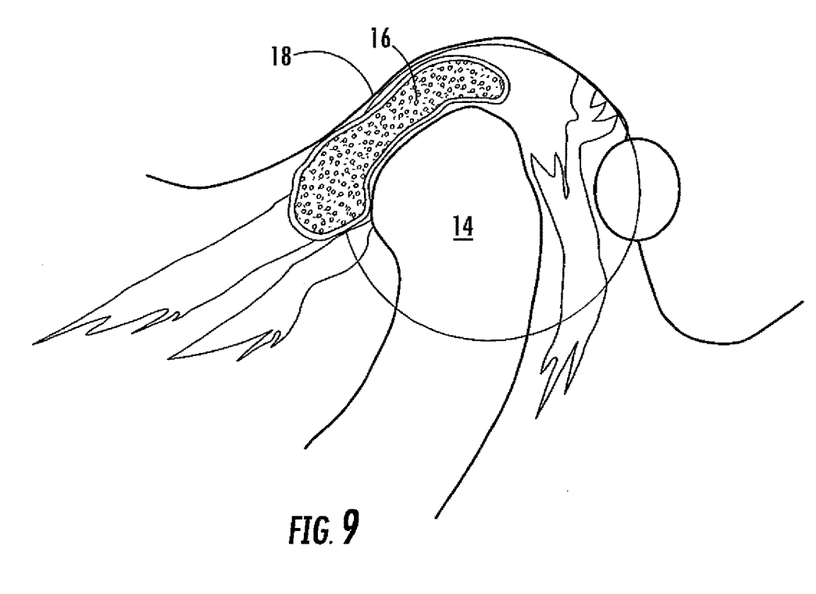
FIG. 9 shows a condyle positioned relative to the temporal bone after repositioning according to the method.

Measured data from the jaw tracking kinesiograph is transmitted to a computer and the data is recorded to determine physiological responses, while the TENS unit simultaneously breaks up pathologic muscle and occlusal engrams. The preferred bite position is determined and fixed. This step allows the clinician to precisely place the left and right condyles 14 on the associated articular discs 16 and braced against the articular eminences 18, as shown in FIG. 9. As compared with the positioning of the condyles and articular discs in FIG. 8, the temporomandibular joint spaces in FIG. 9 are decompressed by the process, and proper spacing between the mandibular condyles and the temporal bones of the skull is created. With the mandible and condyles in this position, the orthotic according to the invention is produced.

Figure 7A:
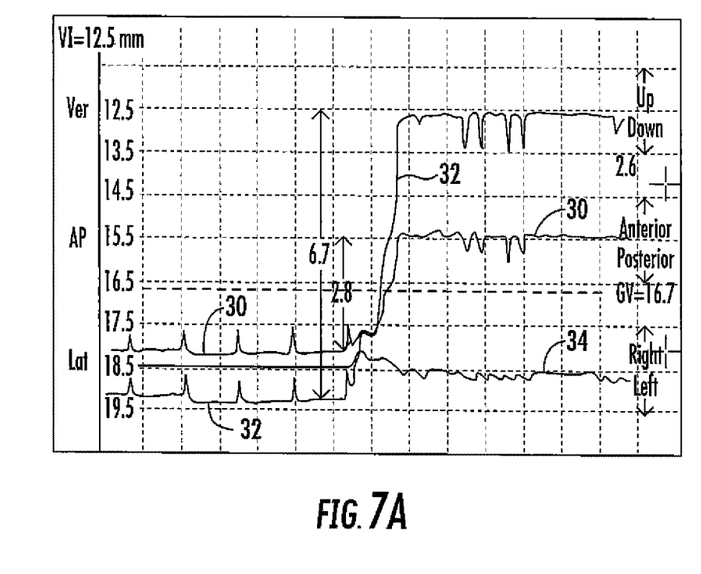
FIG. 7A and FIG. 7B show graphs and readings of the jaw position.

The clinical operator observes the mandibular movements, such as on the computer screen that receives positioning data from the jaw tracking kinesiograph, and determines the required position of the mandible and the associated condyles for the particular subject. FIG. 7A shows the influence of the TENS unit on the position of the mandible. Line 30 shows anterior and posterior movement of the subject's mandible with each electrical pulse. Line 32 shows vertical movement of the mandible with each electrical pulse. Line 34 shows lateral movement of the mandible with each pulse.

The starting position is with the subject's mouth in a relaxed open position. Muscle contractions are initiated from the full resting length of the muscles, as the TENS relaxes the muscle and then contracts. The right portion of FIG. 7A demonstrates the subject closing the mandible on the back teeth and tapping the teeth together.

Figure 7B:
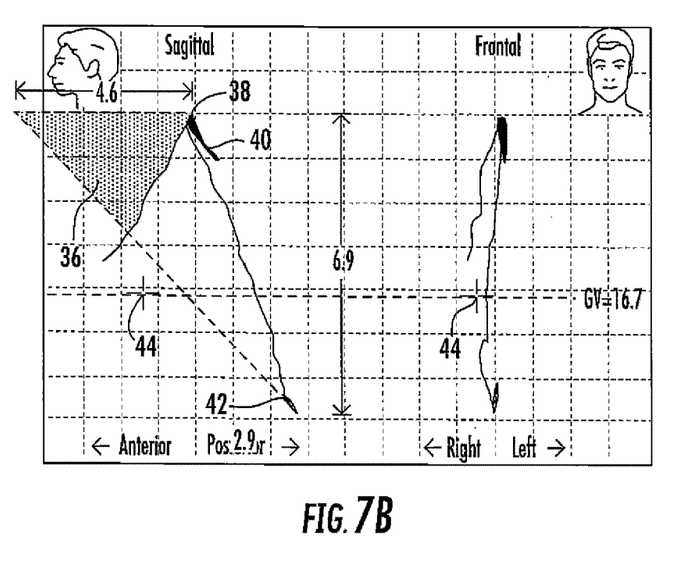

The graphing of FIG. 7A continues at the left side of FIG. 7B. The bite position of the teeth (teeth together) is where Line 32 continues toward shaded triangle 36. The bite is aligned to point 38. Line 40 demonstrates the habitual bite, which is, produced form the tapping of the posterior teeth (right side graphing of FIG. 7A). The movement represented by line 32 creates line 40. For this subject, the bite is over-closed by 3.2 mms (GV=16.7 minus 12.5 starting point). FIG. 7B. "GV" means Golden Vertical, which is the ideal vertical dimension of occlusion (the distance of the upper gum where the gum attaches to the central incisor, down to the region where the lower gum attaches to the lower central incisor). The diagonal line 42 left side of FIG. 7B demonstrates the neuromuscular path of closure of the mandible. The movement represented by line 30 (neuromuscular pulsing) creates line 42. This path a healthy position for closing the mandible after bringing the left and right condyles of TM joints downwards and forwards following recapture of the articular disc.

The images of FIGS. 7A and 7B are the result of tracking the magnet attached to the lower front teeth, and the associated detection of the magnetic field. Because the condyles move downwards and forwards in the TM joints, the body of the mandible necessarily moves forward as well. This explains the difference between to the two trajectories of the lines 40 and 42.

Figure 10:
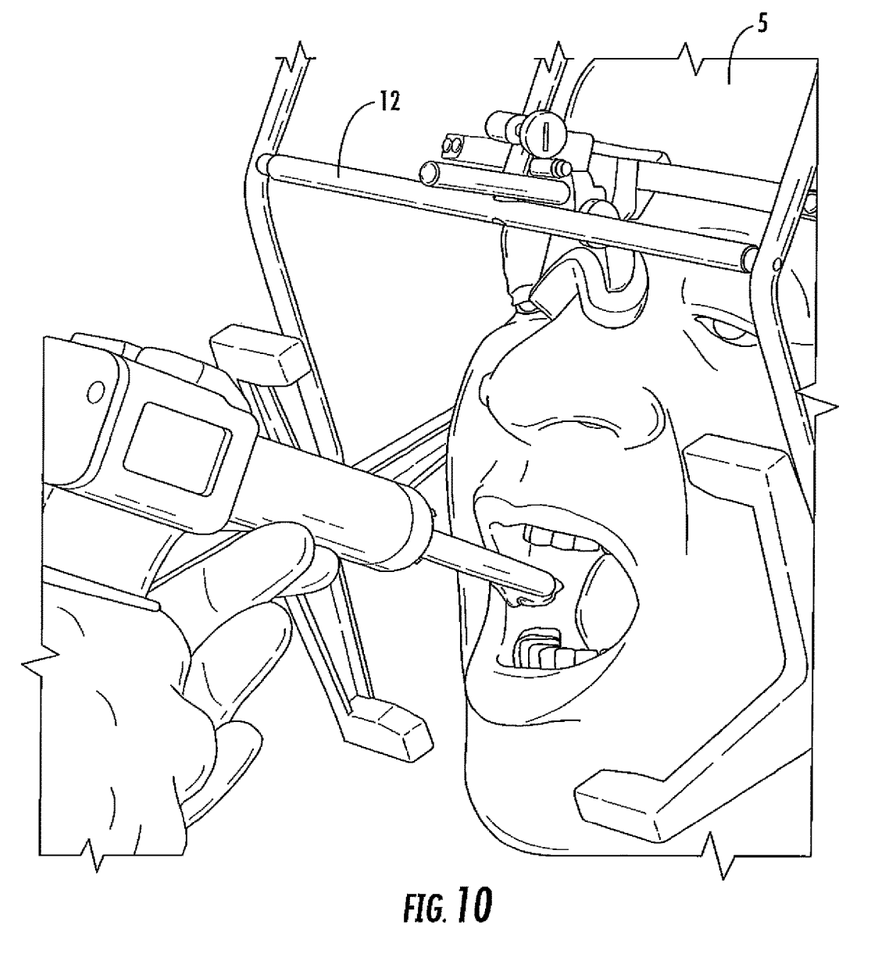
FIGS. 10 and 11 demonstrate taking a bite registration after repositioning of the mandible according to the method.
Figure 11:
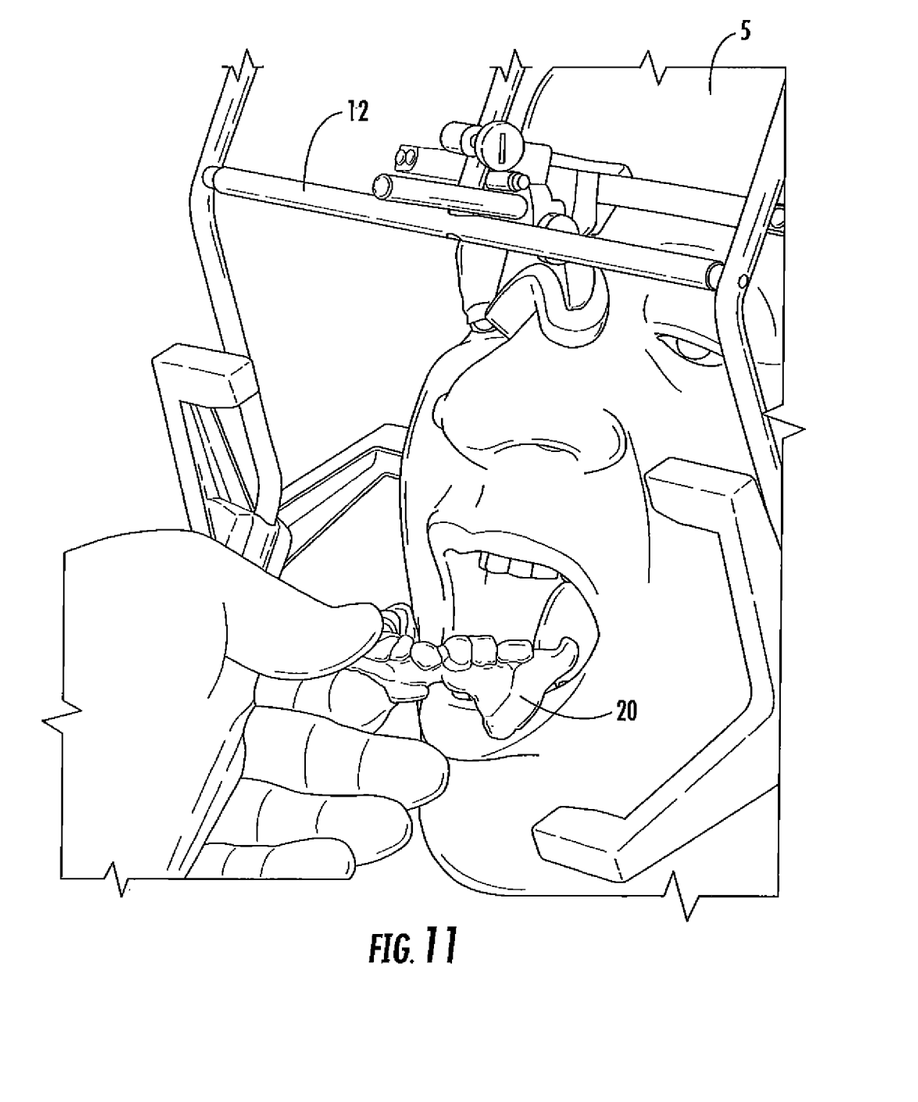

The starting point for the habitual bite is at 12.5 mm. The subject allows his or her jaw to hang and relax. After approximately eight seconds the subject relaxes his or her lips and tongue. This action allows the jaw to float upwardly. Consistent patterns of the cursor (crosshairs) are noted as the jaw closes. A position is noted in taking the bite registration. For the example of FIG. 7B, this position is demonstrated by cursors 44. The subject then opens his or her mouth and bite registration is placed in the mouth and the subject again allows the jaw to close again to this position. FIG. 10; FIG. 11. The orthotic holds the mandible with the indexing within the upper orthotic. In this example, the mandible shifted 1.5 mm forward and 0.5 mm to the right.

Figure 12:
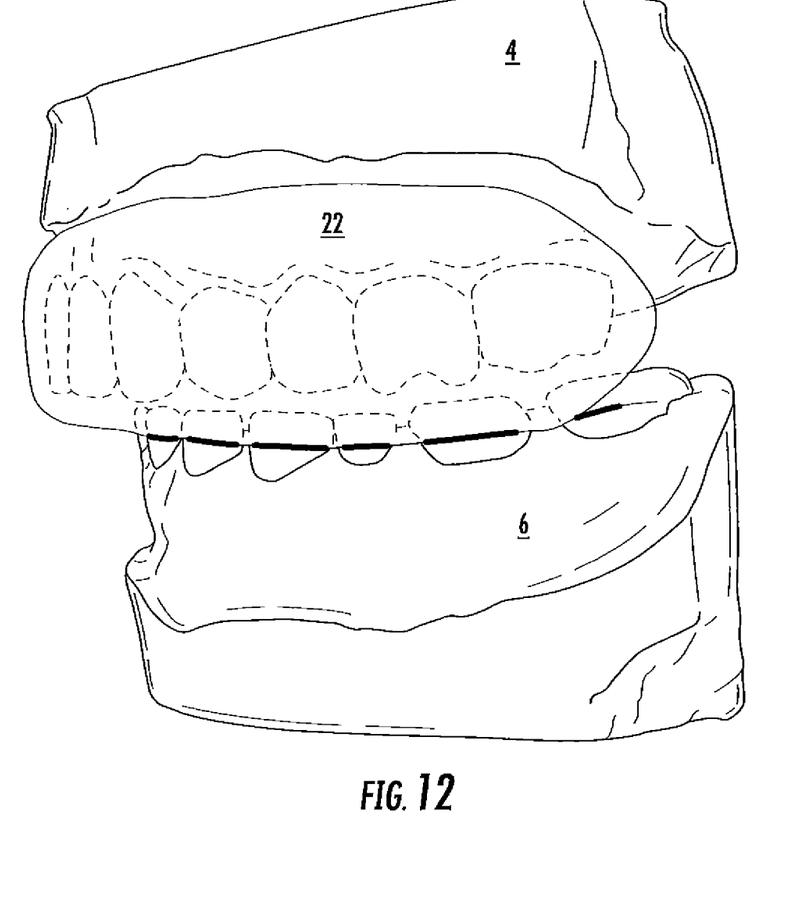
FIG. 12 shows an orthotic produced from the impression of FIG. 11 and positioned on the models of FIG. 2.

The operator records the optimized bite position with, for example, a polyvinylsiloxane bite registration material 20. FIG. 11. The orthotic of the invention is fabricated based upon the recorded optimized position. FIG. 12.

Bite registration, the mandibular scan, the PVS maxillary and mandibular impressions, and a prescription are sent to a laboratory for fabrication of the flexible, resilient maxillary, mandibular, or dual arch concussion orthotic 22. The dental orthotic of the invention is preferred to be fabricated as a unitary member out of a flexible, resilient material. The architecture of the subject's teeth is captured in the orthotic, so that the teeth interdigitate with the corresponding surface of the orthotic. The orthotic is formed to engage the central groove, cusps, grooves and incisal edges of the surfaces of the teeth, as a negative thereof. The upper and lower trays of the orthotic interdigitate with the corresponding teeth to more precisely hold the position of the condyles and articular discs relative to the temporal bone as described herein when the teeth are fully engaged in the upper and lower trays with the jaw closed.

After fabrication, the resulting orthotic is placed in the subject's mouth. Fit and bite are observed and measured, and either verified and/or adjusted according to the bite optimization process. The subject is given instructions on use and maintenance of the concussion orthotic.

The orthotic positions the upper and lower jaws so that the jaws act as a functional unit along with the orthotic. The orthotic is very effective at causing dissipation of, and/or absorbing, concussive forces, both by the orthotic directly absorbing concussive forces, and by the benefits of the orthotic positioning of the upper and lower jaws according to the invention. The required position of the condyles and articular discs relative to the temporal bone to achieve the benefits of the invention is unique to every individual. The process, when properly applied provides, the optimal position of the condyles and articular discs relative to the temporal bone to within 0.1-0.5 mm, and in most cases is within 0.1 to 0.3 mm.

Most commonly, the condyles of the mandible are positioned downwardly and forward to obtain the position required by the invention, with the left and right condyles resting firmly on the respective left and right articular discs of the right and left temporomandibular joints, which also increases the temporomandibular joint spacing. The articular discs are positioned between the condyles and the articular eminences, so that the condyles are braced against the thicker buttressing bone of the articular eminences. FIG. 9. The required mandibular position is maintained by the unitary, flexible and resilient orthotic device produced according to the method of the invention, with the mandibular teeth firmly indexed into the maxillary, mandibular, or dual arch concussion orthotic. The orthotic holds the required position of the mandible and associated condyles while the wearer undergoes strenuous physical activity, thereby reducing the likelihood of concussion due to forces on the mandible.

In use, the maxillary, mandibular, or dual arch concussion orthotic is placed over the teeth of the upper and/or lower jaw. The jaw is closed to form and hold the optimized position determined by the process described above. The biting surface of the concussion orthotic is indexed to receive the upper and/or lower teeth. By interdigitating the upper and/or lower teeth firmly into the orthotic, the condyles 14 of the mandible are firmly positioned on the articular discs 16 of the right and left temporomandibular joints, and are braced against the thicker buttressing bone of the articular eminences 18, reproducing the position of FIG. 9 each time the orthotic is worn. This mandibular position, with the teeth firmly indexed into the concussion orthotic and held in position by the unitary orthotic, results in the optimal position of the upper and lower jaws, which act as a functional unit due to the presence of the properly positioned orthotic. The device, when properly used, is very effective at preventing lateral or compressive movements of the mandible, and in dissipating concussive forces. The optimal position of the mandible relative to the maxilla to achieve this unexpected result is unique to every individual.

Figure 13:
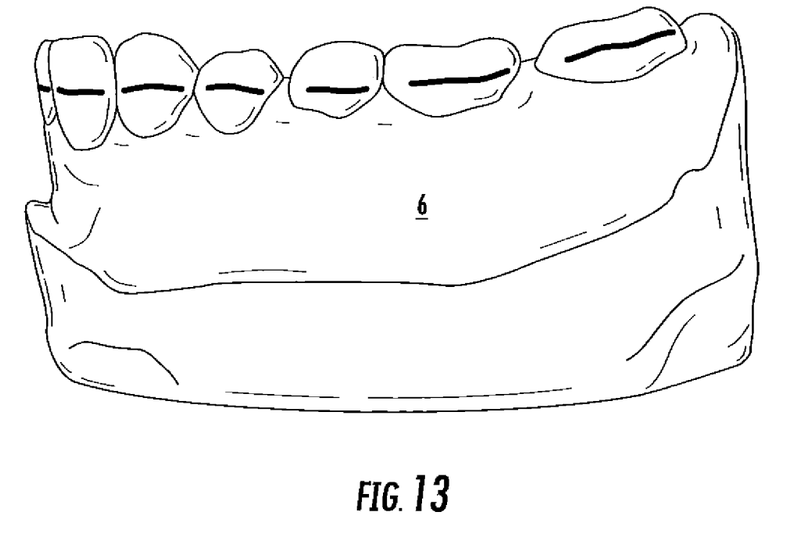
FIG. 13 demonstrates the depth to which the clinical crown of the mandibular teeth is positioned within the orthotic.

The embodiment of the orthotic shown in FIG. 12 is a designated as a maxillary orthotic. A maxillary orthotic fits firmly over the teeth of the maxilla. In a preferred embodiment, the orthotic is fits tightly against the teeth and the gums of the maxilla, and must be manually pulled from the maxilla to dislodge the orthotic. The combination of friction and a vacuum created by the frictional fit, and sealed by moisture from saliva, provide a firm fit. However, while upper, maxillary portion fits tightly, and is preferred to cover substantially the entire length of the maxillary teeth and a portion of the gums as shown in FIG. 12, the lower, mandibular teeth fit more loosely within the orthotic. It is preferred that the orthotic cover about the upper half of the clinical crown of the mandibular teeth, with a portion of the lower mandibular teeth not covered. An exemplary depth of the teeth in the mandibular portion of the orthotic is indicated by the generally horizontal markings on the mandibular teeth shown in FIG. 12 and FIG. 13. For an adult, the depth of the indexing in the lower tray of the orthotic will be at least 4 mm. The result is that the with the maxillary orthotic, the fit is such that when the mouth is opened, the orthotic remains attached to the maxilla, but the orthotic pulls away from the mandibular teeth. The user is able to talk with this structure of the device. The user may then reposition the mandibular teeth in the orthotic by closing his or her mouth, which also positions the condyles against the buttress bone, recapturing the articular disc with articular disc positioned between the condyle and the buttress bone. This position disputes concussive forces anteriorly through the buttress bone to the zygomatic arches and away from the cranial vault.

The natural reaction to imminent impact about the head or face is to clench the jaw. Accordingly, the orthotic forms the maxilla and mandible as a unit, while also providing cushion between the maxilla and mandible, and providing force absorption and force dissipation. The orthotic also positions the condyles as described above for retarding concussion.

A mandibular orthotic may also be prepared, wherein the lower, mandibular portion fits tightly, and the upper, maxillary teeth fit more loosely within the orthotic. The same frictional and vacuum fit principle is applied to the mandibular portion of the orthotic. In this case, the orthotic remains attached to the mandible when the jaw and mouth are opened, but the orthotic pulls away from the maxillary teeth when the jaw is opened. The user is able to talk with this structure of the device. The orthotic also positions the condyles as described above for retarding concussion when the jaw is closed again.

A dual arch orthotic may also be prepared that firmly holds both the maxilla and the mandible. The lower, mandibular portion fits tightly, and the upper, maxillary teeth fit also fit tightly within the orthotic. The same frictional and vacuum fit principle is applied. In this case, the orthotic remains attached to the maxilla and the mandible when the jaw and mouth are opened, but may release slightly from the mandible. The user is not able to talk with this structure of the device. The orthotic also positions the condyles as described above for retarding concussion.

In all three versions of the orthotic, the device is unitary where it covers the maxillary central incisors and the mandibular central incisors. It is preferred that there is no separation or gap in the orthotic between the upper portion or upper tray that receives the maxillary incisors and the lower portion or lower tray that receives the mandibular incisors, and the orthotic is therefore unitary. Prior devices provide separate units for the maxilla and the mandible, or the device or appliance is linked at the rear, but is not unitary (does not separate) at the trays that received the upper and lower incisors. The orthotic of the present invention prevents lateral movement of the mandible that is allowed by prior art devices that do not have the unitary construction at an anterior portion of the device. The orthotic of the present invention locks occlusion and prevents freedom of movement when the jaw is closed, whereas other devices permit movement of the mandible relative to the maxilla when the teeth .are engaged in those appliances.

The orthotic is formed to be resilient and energy absorbing. In one embodiment, the thickness of the material when formed into the orthotic ranges from 4-8 millimeters. The orthotic may be formed of a material comprising a copolymer of ethylene vinyl acetate, such as ERKOFLEX, and including laminates.

What is claimed:

1. A method of producing a concussion retarding dental orthotic, comprising steps of:
positioning a condyle and an articular disc of a right temporomandibular joint from a position wherein the condyle of the right temporomandibular joint is exposed to a bone of a right articular eminence to a position wherein the condyle of the right temporomandibular joint rests firmly on the articular disc of the right temporomandibular joint, with the articular disc of the right temporomandibular joint braced against the bone of the right articular eminence;

positioning a condyle and an articular disc of a left temporomandibular joint from a position wherein the condyle of the left temporomandibular joint is exposed to a bone of a left articular eminence to a position wherein the condyle of the left temporomandibular joint rests firmly on the articular disc of the left temporomandibular joint, with the articular disc of the right temporomandibular joint braced against the bone of the left articular eminence;

taking a bite registration and capturing structure of maxillary teeth and mandibular teeth and capturing a relative position of the maxillary teeth to the mandibular teeth while the condyle of the right temporomandibular joint rests firmly on the articular disc of the right temporomandibular joint with the right articular disc braced against the bone of the right articular eminence, and the condyle of the left temporomandibular joint rests firmly on the articular disc of the left temporomandibular joint with the left articular disc braced against the bone of the left articular eminence;

subsequently forming from the bite registration a resilient dental orthotic;

placing the resilient dental orthotic to receive the maxillary teeth and the mandibular teeth; holding, by the resilient dental orthotic, a mandible in position relative to a maxilla so that the condyle of the right temporomandibular joint rests firmly on the articular disc of the right temporomandibular joint with the right articular disc braced against the bone of the right articular eminence and the condyle of the left temporomandibular joint rests firmly on the articular disc of the left temporomandibular joint while the left articular disc braced against the bone of the left articular eminence.

2. A method of producing the concussion retarding dental orthotic as described in claim 1, further comprising a step of electrically stimulating head and neck muscles prior to the steps of positioning the condyle of the right temporomandibular joint to rest firmly on the articular disc of the right temporomandibular joint with the right articular disc braced against the bone of the right articular eminence and positioning the condyle of the left temporomandibular joint to rest firmly on the articular disc of the left temporomandibular joint with the left articular disc braced against the bone of the left articular eminence.

3. A concussion retarding dental orthotic produced by the method of claim 2.

4. A method of producing the concussion retarding dental orthotic as described in claim 1, further comprising a step of positioning the condyle of the right temporomandibular joint to rest firmly on the articular disc of the right temporomandibular joint, with the right articular disc braced against the bone of the right articular eminence using a jaw tracking kinesiograph and further comprising a step of positioning the condyle of the left temporomandibular joint to rest firmly on the articular disc of the left temporomandibular joint, with the left articular disc braced against the bone of the left articular eminence using a jaw tracking kinesiograph.

5. A concussion retarding dental orthotic produced by the method of claim 4.

6. A method of producing the concussion retarding dental orthotic as described in claim 1, further comprising a step of stimulating head and neck muscles with a transcutaneous electrical neural stimulator prior to the step of positioning the condyle of the right temporomandibular joint to rest firmly on the articular disc of the right temporomandibular joint with the right articular disc braced against the bone of the right articular eminence and the step of positioning the condyle of the left temporomandibular joint to rest firmly on the articular disc of the left temporomandibular joint with the left articular disc braced against the bone of the left articular eminence.

7. A concussion retarding dental orthotic produced by the method of claim 6.

8. A method of producing the concussion retarding dental orthotic as described in claim 1, further comprising a step of electrically stimulating head and neck muscles, a step of positioning the condyle of the right temporomandibular joint to rest firmly on the articular disc of the right temporomandibular joint with the right articular disc braced against the bone of the right articular eminence using a jaw tracking kinesiograph, and a step of positioning the condyle of the left temporomandibular joint to rest firmly on the articular disc of the left temporomandibular joint with the left articular disc braced against the bone of the left articular eminence using a jaw tracking kinesiograph.

9. A concussion retarding dental orthotic produced by the method of claim 8.

10. A method of producing the concussion retarding dental orthotic as described in claim 1, wherein the dental orthotic is constructed and arranged to receive the maxillary teeth in an upper tray portion of the dental orthotic and the dental orthotic is constructed and arranged to receive the mandibular teeth in a lower tray portion of the dental orthotic, and wherein the upper tray portion of the dental orthotic is retained on the maxillary teeth by frictional fit and the lower tray portion of the dental orthotic is not retained on the mandibular teeth when the mandible moves away from the maxilla as a jaw is opened.

11. A concussion retarding dental orthotic produced by the method of claim 10.

12. A method of producing the concussion retarding dental orthotic as described in claim 1, wherein the dental orthotic is constructed and arranged to receive the maxillary teeth in an upper tray portion of the dental orthotic and the dental orthotic is constructed and arranged to receive the mandibular teeth in a lower tray portion of the dental orthotic, and wherein the upper tray portion of the dental orthotic is retained on the maxillary teeth by frictional fit and the lower tray portion of the dental orthotic is not retained on the mandibular teeth when the mandible moves away from the maxilla as a jaw is opened, and wherein the mandibular teeth are repositioned within the lower portion of the dental orthotic when the jaw is closed so that the unitary, flexible and resilient dental orthotic holds the mandible in position relative to the maxilla and the right temporomandibular joint rests firmly on the articular disc of the right temporomandibular joint with the right articular disc braced against the bone of the right articular eminence and the condyle of the left temporomandibular joint rests firmly on the articular disc of the left temporomandibular joint while the left articular disc braced against the bone of the left articular eminence.

13. A concussion retarding dental orthotic produced by the method of claim 12.

14. A method of producing the concussion retarding dental orthotic as described in claim 1, wherein the dental orthotic is unitary where an upper tray portion of the dental orthotic is constructed and arranged to receive maxillary teeth and a lower tray portion of the dental orthotic is constructed and arranged to receive mandibular teeth.

15. A method of producing the concussion retarding dental orthotic as described in claim 1, wherein an upper tray portion of the dental orthotic is constructed and arranged to receive maxillary teeth and a lower tray portion of the dental orthotic is constructed and arranged to receive mandibular teeth, and the dental orthotic is constructed and arranged to cover all of the anterior clinical crown of maxillary incisors and less than all of the clinical clown of the mandibular incisors.

16. A concussion retarding dental orthotic produced by the method of claim 15.

17. A method of producing the concussion retarding dental orthotic as described in claim 1, wherein the dental orthotic is unitary where an upper tray portion of the dental orthotic is constructed and arranged to receive maxillary teeth and a lower tray portion of the dental orthotic is constructed and arranged to receive mandibular teeth, and the dental orthotic is constructed and arranged to cover all of the anterior clinical crown of maxillary incisors and less than all of the clinical clown of the mandibular incisors.

18. A method of producing the concussion retarding dental orthotic as described in claim 1, wherein the dental orthotic is constructed and arranged to receive the maxillary teeth in an upper tray portion of the dental orthotic and the dental orthotic is constructed and arranged to receive the mandibular teeth in a lower tray portion of the dental orthotic, and wherein the lower tray portion of the dental orthotic is retained on the mandibular teeth by frictional fit and is not retained on the mandibular teeth when the mandible moves away from the maxilla as a jaw is opened.

19. A method of producing the concussion retarding dental orthotic as described in claim 1, wherein the dental orthotic is constructed and arranged to receive the maxillary teeth in an upper tray portion of the dental orthotic and the dental orthotic is constructed and arranged to receive the mandibular teeth in a lower tray portion of the dental orthotic, and wherein the dental orthotic is retained on the mandibular teeth and the maxillary teeth by frictional fit.

20. A concussion retarding dental orthotic produced by the method of claim 1.

* * * * *